United States Patent [19]
King

[11] Patent Number: 5,738,087
[45] Date of Patent: Apr. 14, 1998

[54] AEROSOL MEDICATION DELIVERY SYSTEM

[76] Inventor: Russell W. King, 4501 Littlejohn St., Baldwin Park, Calif. 91706

[21] Appl. No.: 766,812

[22] Filed: Dec. 13, 1996

Related U.S. Application Data

[63] Continuation-in-part of Ser. No. 531,697, Sep. 21, 1995, Pat. No. 5,617,844.

[51] Int. Cl.⁶ ........................................... A61M 11/00
[52] U.S. Cl. ........................ 128/200.23; 128/205.24; 128/203.24; 137/527; 137/527.8
[58] Field of Search ............. 128/200.14, 200.23, 128/205.24, 207.12, 203.24; 137/511, 527, 527.8

[56] References Cited

U.S. PATENT DOCUMENTS 3,809,119  5/1974  Cave ........................ 137/527.8
4,063,570  12/1977  Mitchell et al. ............. 137/454.2
4,201,241  5/1980  Schertler ..................... 137/527

Primary Examiner—Vincent Millin
Assistant Examiner—William J. Deane, Jr.
Attorney, Agent, or Firm—James E. Brunton, Esq.

[57] ABSTRACT

An apparatus for use in conjunction with a multi-dose inhaler which includes a novel valving mechanism and an expansion chamber which permits medication to be delivered to the patient without the need for precise timing of canister actuation. The apparatus also includes a filter unit for filtering the patient's exhaled breath and also includes a unique baffling arrangement which functions to decrease average aerosol particle size for better targeting the desired lung area. In one form of the invention, the valving mechanism comprises an apertured elastomeric valve member having a top pivot bar which uniquely pivots on a pair of pivot posts provided on proximate the upper margin of a novel valve member engaging, generally planar base.

18 Claims, 10 Drawing Sheets

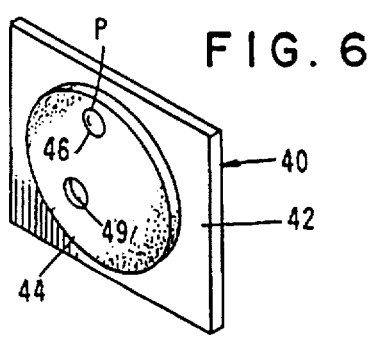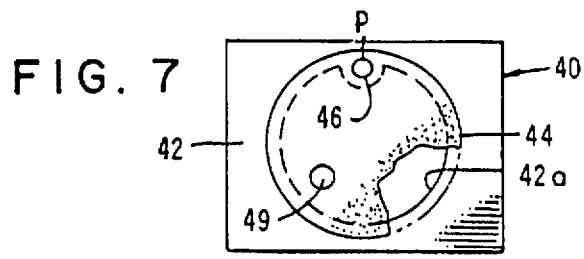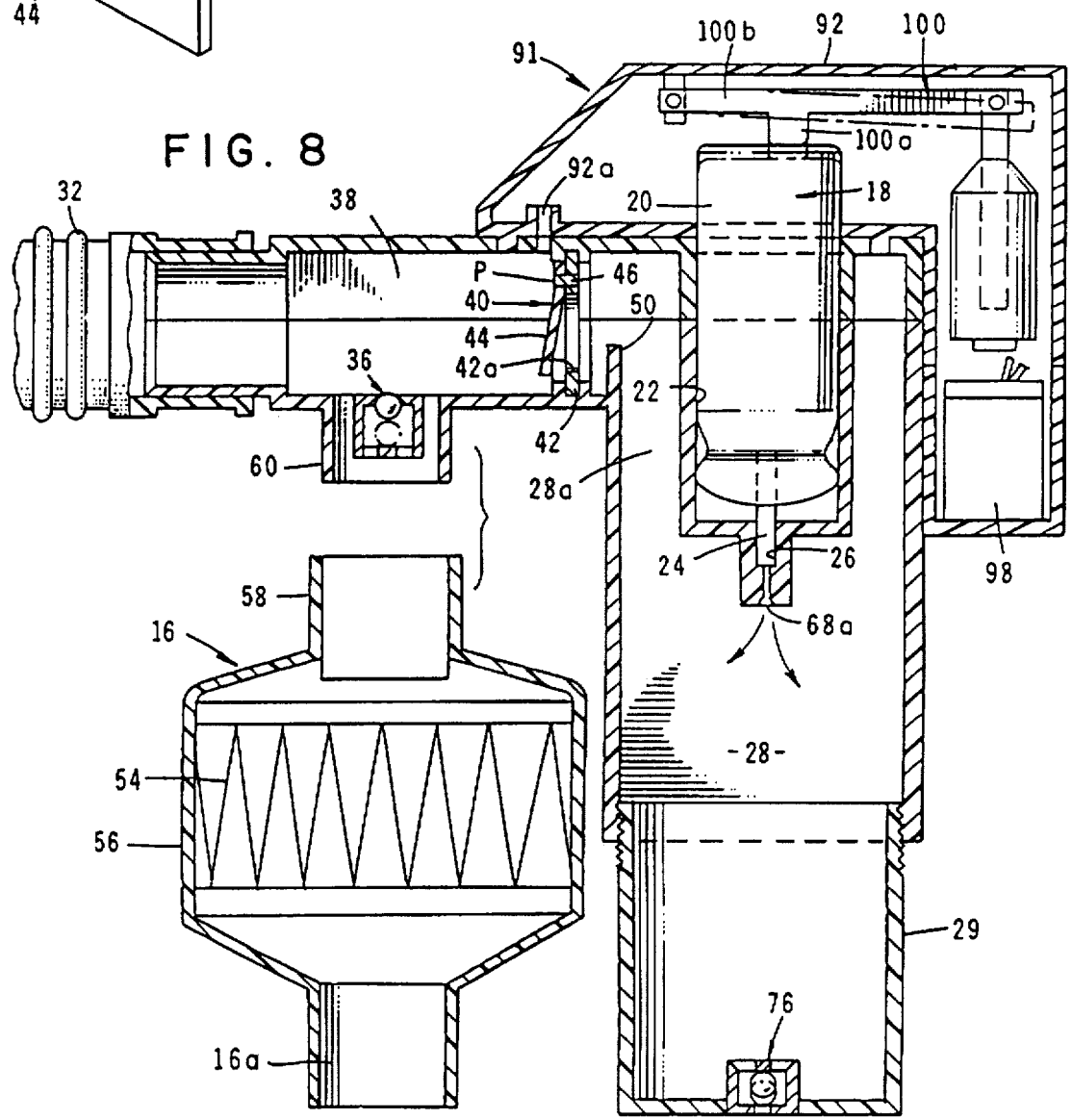

AEROSOL MEDICATION DELIVERY SYSTEM

SPECIFICATION

This is a Continuation-In-Part of application Ser. No. 08/531,697 which was filed Sep. 21, 1995, now U.S. Pat. No. 5,617,844.

BACKGROUND OF THE INVENTION

1. Field of the Invention

The present invention relates to aerosol medication delivery systems. More particularly, the invention concerns an improved aerosol inhalation apparatus that is very useful for dispensing pharmaceuticals in the treatment of respiratory or pulmonary diseases and for systemic delivery of drugs via aerosolization.

2. Discussion of the Prior Art

Therapeutic aerosols are commonly administered to patients suffering from numerous types of pulmonary diseases. Specific medications, include $beta_2$ agonists, anticholinergies, cromolyn sodium, and steroids. More recently the aerosol method of delivery has been used to administer Pentamidine to patients afflicted with AIDS, and is presently under consideration as a delivery means for insulin in the treatment for diabetes. Experience has shown that the use of aerosols to treat lung disease is highly advantageous in that it produces optimal therapy with minimum side effects. Both physical and clinical factors affect aerosol deposition in the lungs. Physical factors include inertial impaction, sedimentation, and diffusion. Clinical factors include particle size, ventilatory pattern and lung function. Aerosols larger than 5 micron aerodynamic diameter (AD) poorly penetrate the upper respiratory tract. Those in the 0.2 to 2 micron range tend to have their maximum disposition in the lung parenchyma.

In general the devices used for producing medical aerosols fall into three categories; the small volume nebulizer (SVN), the metered dose inhaler (MDI), and the powder dose inhaler (PDI). Although the small volume nebulizer (SVN) has traditionally been the apparatus of choice for delivery of therapeutic aerosols, many institutions are now switching to the MDI. The small volume nebulizer (SVN) apparatus typically consists of disposable or reusable nebulizer, a mouthpiece or facemask, and a pressurized gas source usually oxygen or air. The metered dose inhaler (MDI), on the other hand typically contains the active drug, a metering valve, and a chlorofluorcarbon (CFC) propellants. The drug containing canister of the device is generally fitted to a mouthpiece actuator, and activation by compression of the canister into the mouthpiece results in the release of a unit does of medication.

There is extensive literature indicating the successes of aerosol therapies, as well as the difficulties of using the aerosols properly. See, for example, Respiratory Infection: Diagnosis and Management. J. E. Pennington ed. Raven Press, N.Y. chest 1981, 80:911–915; Arch. Int. Med. 1973, 131:88–91. Notwithstanding the very considerable development of aerosols and methods of using the same, there is still room for improvement in the administration of pharmaceutical aerosols.

A major problem of aerosol therapy is to deposit the aerosol on the walls of small bronchi and bronchioles, where the action of the medication is most often required. Less than 10% of the medication delivered by standard multi-dose inhalers reaches the typical patient's lungs. Most of the 90% of the medication which does not penetrate the target area is deposited in the mouth, throat, and trachea, and is eventually ingested. A small fraction of the aerosol is exhaled.

For effective utilization, the aerosol should consist of small particles, less than 5 microns AD, since larger particles cannot negotiate the sharp turns to the lung and are deposited in the orophapynx due to inertial effects. In order to minimize mouth deposition further it has been shown that the volumetric flow rate of the inhaled aerosol should be below 30 liters per minute. Meter dose inhalers deliver aerosol at a high initial velocity directly into the patent's mouth. This high initial velocity of the aerosol is a major factor in the ineffectiveness of many inhaler systems.

Another serious problem inherent in MDI aerosol medication is patient timing coordination. If patient inhalation does not occur on a timely basis with MDI canister actuation, a large percentage of the medication is lost.

Several pharmaceutical manufacturers have included, or sold separately with their MDI aerosol products, what are referred to variously as "spacers", "oral adapters", and "space-inhalers", and "spray inhalers" to be used in conjunction with their products. These offer only a partial solution to the problems which typically occur in MDI aerosol delivery.

The apparatus of the present invention provides a very substantial improvement over all prior art MDI-type devices in that it addresses: (1) volumetric flow rate of medication, (2) elimination of patient coordination problems, (3) particle size and (4) environmental protection considerations.

SUMMARY OF THE INVENTION

It is an object of the present invention to provide an inhalation apparatus, which, when used with an MDI-type inhaler, will result in a substantial increase in the delivery to the patient of particles in the respirable size range.

Another object of the invention is to provide an apparatus of the aforementioned character which essentially eliminates patient timing coordination problems when administering a unit does of medication.

Another object of the invention is to provide an apparatus which limits volumetric flow rate of the inhaled aerosol to that of normal patient breathing, i.e. below 30 liters per minute.

Another object of the invention is to provide a novel apparatus wherein release of medication from the MDI canister is triggered automatically by patient exhalation rather than by manual actuation, thereby providing for timely accessibility during the next inhalation.

Yet another object of the invention is to provide an apparatus of the character described wherein the number of desired patient inhalations can be preselected, and wherein medication availability will automatically terminate upon reaching that number.

Still another object of the invention is to provide an apparatus as described in the preceding paragraphs wherein air exhaled from the patient is safely filtered before it is released to room atmosphere.

BRIEF DESCRIPTION OF THE DRAWINGS

FIG. 6 is a generally perspective view of an alternate form of flow control means.

FIG. 7 is a front view of the flow control means shown in FIG. 6 partly broken away to show the valve seat.

FIG. 8 is a cross-sectional view of an alternate form of the inhalation apparatus of the invention.

DESCRIPTION OF THE INVENTION

Figure 1:
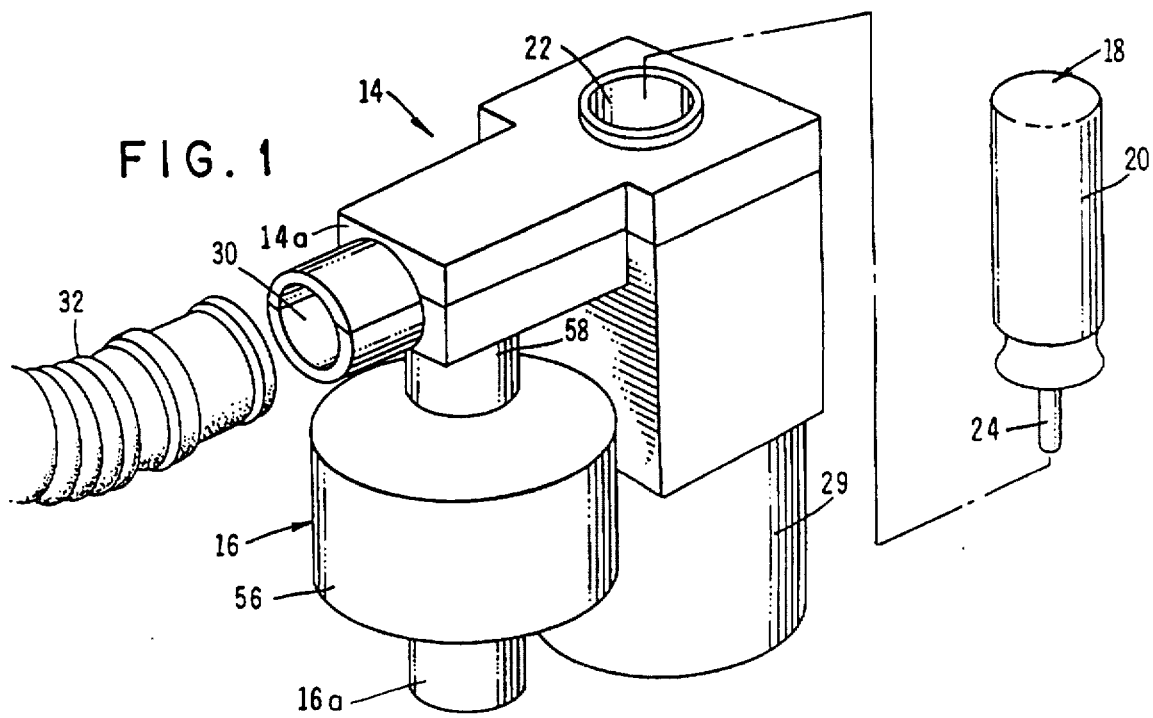
FIG. 1 is a generally perspective view of one form of the inhalation apparatus of the invention.
Figure 2A:
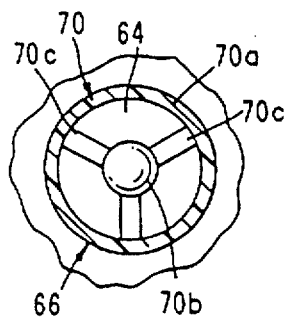
FIG. 2 is a generally perspective, exploded view of the apparatus shown in FIG. 1.
Figure 3:
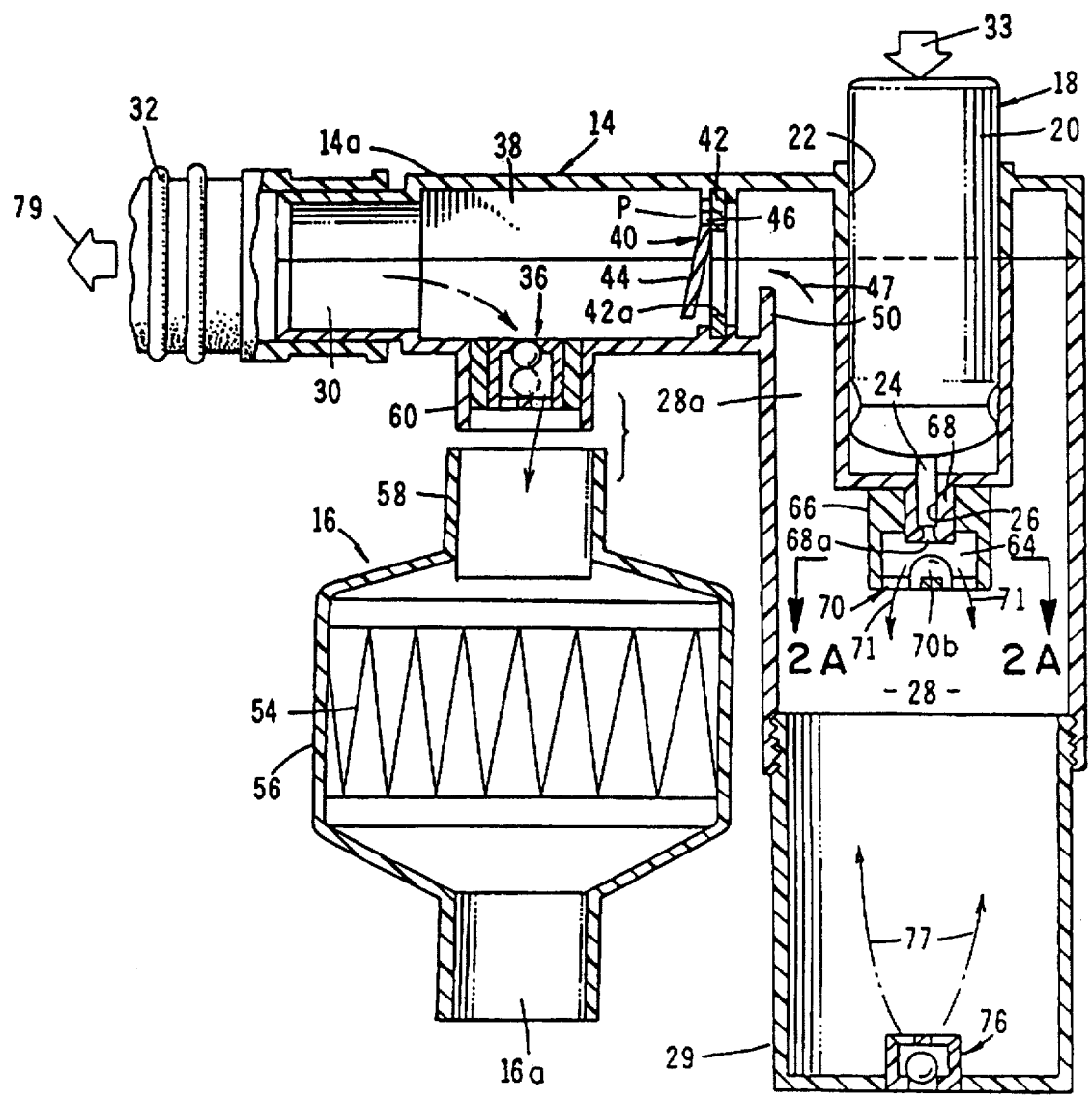
FIG. 3 is an enlarged, cross-sectional view of the apparatus shown in FIG. 1.
Figure 2:
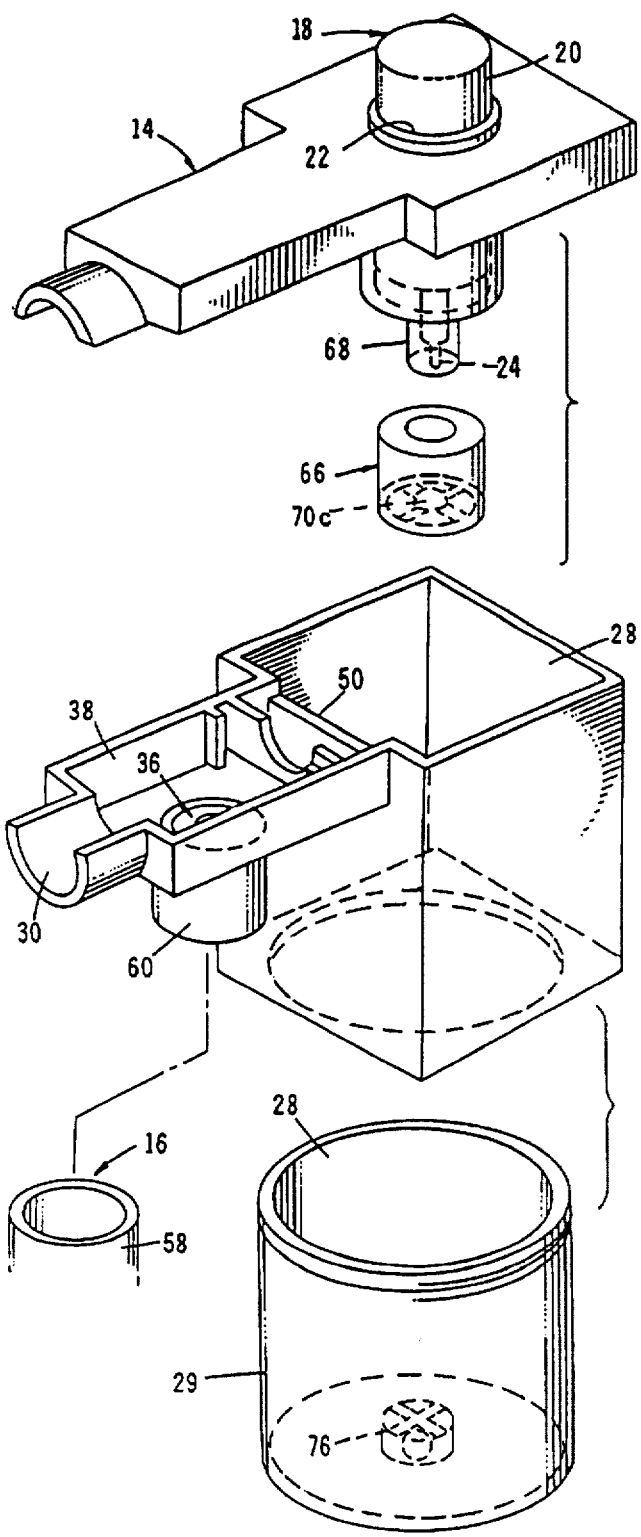

Referring to the drawings and particularly to FIGS. 1, 2, and 3, the aerosol inhalation apparatus of one form of the present invention can be seen to comprise a sectionalized main housing 14 to which is attached filtering means here provided as a bacteria filter assembly 16 and a drug nebulizing means, shown here as a standard, commercially available aerosolized multi-dose inhaler (MDI) 18 which is charged with a suitable propellant. As best seen in FIGS. 1 and 3, multi-dose inhaler 18 includes a canister 20 which is removably receivable within an easily accessible chamber 22. Inhaler 18 also includes an actuator 24 which is receivable into an entrance orifice 26 which is in communication with a first, or expansion chamber 28 via a defuser means, the character of which will presently be described. Provided proximate the first end 14a of housing 14 is inhalation means comprising a standard size breathing port 30 which is coupled with the patient via a flexible conduit 32 and an appropriate mouthpiece, or face mask (not shown). In a manner presently to be described, the various components and interconnecting fluid flow passageways of the device are uniquely constructed and arranged to maximize the delivery of properly sized aerosolized medication to the patient on a timely basis.

Turning particularly to FIG. 3, it can be seen that the nebulizing means, or MDI 18 of the apparatus is mounted within chamber 22 in a manner such that when a downward force is exerted on canister 20 in the direction of the arrow 33. The propellant contained within the MDI will cause a fine particle-laden spray to be emitted from actuator 24. This spray comprises a multiplicity of medicament particles of various sizes under pressure into expansion chamber 28. As previously mentioned the multi-doses inhaler is of a standard construction well known to those skilled in the art.

The plume of aerosolized medicament which nominally has a release volume of on the order of 10–20 milliliters (mL) is composed largely of a rapidly evaporating propellant, so that it readily expands into the confines of expansion chamber 28. Chamber 28 is designed with a volume capacity of on the order of 200–250 mL so that upon tidal volume patient breathing essentially all the medication contained within the aerosolized plume will be inhaled from the chamber.

During use of the apparatus in patient treatment the patient's exhaled air is received by filter assembly 16 via a first valve means, shown here as a one-way ball check valve 36 of standard construction. During patient exhalation, a nominal amount of resistance to air flow is caused by valve 36 which creates a slight over pressure in a second forward chamber 38, thereby maintaining the novel flow control means 40 in a closed position. Accordingly, if the MDI is actuated during patient exhalation, the aerosolized medicament is securely contained with expansion chamber 28 for use during the next patient inhalation.

Upon patient inhalation, one-way valve 36 securely closes and the flow control means 40, shown here as a one-way diaphragm type valve opens so that all medication from chamber 28 is carried through chamber 38 and into the patient's lungs via conduit 32 and the mouthpiece or face mask. If the MDI is actuated during the time of patient inhalation the medication will, of course, enter the air stream and flow directly to the patient's lungs. Thus, the system as described uniquely provides for delivery of the desired patient dose with no concern as to the timing of medication release from the MDI device. Also, the flow rate of medication to the patient is strictly a function of patient breathing only, thereby optimally allowing the medication to clear the patient's throat area and flow freely into the patient's lower lung compartments.

Figure 4:
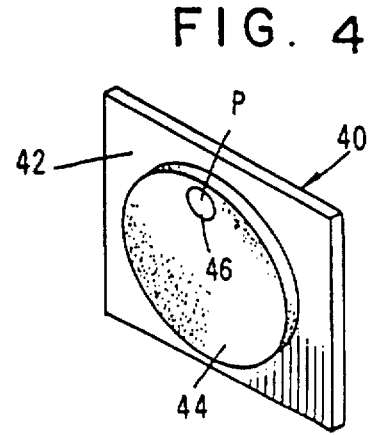
FIG. 4 is an enlarged, generally perspective view of one form of the flow control means of the apparatus.
Figure 5:
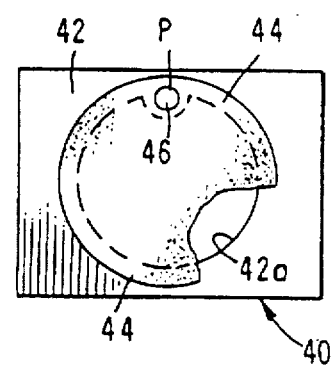
FIG. 5 is a front view of the flow control means shown in FIG. 4 partly broken away to show the valve seat.

As best seen in FIGS. 4 and 5, one form of the flow control means 40 comprises a base wall 42 having a central opening 42a therethrough (FIG. 5). Affixed to wall 42 at a single pivot point P is a generally circular, substantially flexible diaphragm or valve member 44. Member 44 can be constructed of various materials including plastic and a number of different types of yieldably deformable elastomeric and polymeric materials. Pivot point P is defined by a fastener such as rivet 46 (FIG. 3) which passes through member 44 at a location proximate its outer periphery and then through base wall 42 in the manner shown in FIGS. 3, 4, and 5. With this unique construction, fluid passing through passageway 28a in the direction of the arrow 47 of FIG. 3 will flow through aperture 42a and will cause member 44 to open in a novel pivoting motion about pivot point P. As a result of this novel design, resistance to aerosol flow through the flow control means is less than 5% of that caused by standard commercially available, one-way valves. Therefore, since this small resistance is the only impediment to aerosol flow during patient inhalation, essentially no medication is lost due to the recombining of the aerosolized particles.

Optionally, the flexible diaphragm or flapper member of the flow control means can be provided with a small aperture 49 of the character shown in FIGS. 6 and 7. In this alternate embodiment of the invention, the diaphragm 44 is affixed to the base wall 42 in the same manner as previously described and pivots about pivot point P defined by a rivet 46. With this construction, upon patient exhalation a small portion of the moisture-laden exhaled air will be permitted to enter chamber 28 via aperture 49 and mix with the dry air therein, thusly reducing medicament loss due to particulate static charge.

Connected to chamber 28 and in communication therewith is settling means shown here as a settling chamber 29 which is threadably connected to housing 14 and which functions to remove large particles from the particulate laden mist by means of sedimentation. The provision of a baffle means, here comprising an upstanding wall 50 (FIGS. 2 and 3) which interferes with the flow of the larger particles also contributes to the reduction of the number of large particles contained within the particulate laden spray which reach the patient.

As previously mentioned, it is important to note that the apparatus will function equally well with or without filter assembly 16. In those instances where medicament should not be released to the environment, a filter means such as filter assembly 16 can be provided to filter particles from the spray flowing into chamber 38 as a result of patient exhalation. In the embodiment of the invention shown in FIGS. 1, 2, and 3, filtering assembly 16 is made up of a filtering element 54, which is retained within a housing 56. Housing 56 includes a neck portion 58 which is slidably receivable over a cylindrical skirt 60 which communicates with chamber 38 via valve 36 and which forms a part of housing 14. Filtering element 54 is of a character well known to those skilled in the art and is commercially available from sources such as Intertech of Lincolnshire, Ill.

In operating the apparatus of the invention shown in FIGS. 1 through 5, the commercially available multi-does inhaler 18 is first inserted into chamber 22 in the inverted position shown in FIG. 3 so that actuator 24 is received within entrance orifice 26. A downward force is then exerted on the aerosolized MDI in the direction of the arrow 33 of FIG. 3. This causes the propellant within the MDI canister to force a medicament laden mist to plume outwardly of actuator 24 and into a small chamber 64 which is provided in a housing 66 that forms a part of the diffusion means of the present invention. Housing 66 has a central bore that is receivable over a stem 68 provided proximate the base of chamber 22. Stem 68 includes an aperture 68a which communicates with chamber 64 in the manner best seen in FIG. 3. Turning also to FIG. 2A, disposed in the outlet portion of chamber 64 is a diffusor element 70 which comprises an outer ring portion 70a and a central, generally hemispherically shaped diffusor member 70b which is held centrally of ring 70a by means of a plurality of spoke-like support elements 70c. With this construction, as the particulant laden mist flows outwardly of aperture 68a it will impinge upon hemispherical diffusor element 70b and will be directed inwardly between support members 70c in the manner indicated by the arrows 71 of FIG. 3. The thusly difused particulant laden mist will enter expansion chamber 28 causing the chamber to partially fill with the particulant laden mist. The primary function of the diffuser element 70 is to cause larger aerosol particles being emitted from the MDI canister to further subdivide through impaction into much smaller, clinically useful, particles. As the mist, under pressure, enters expansion chamber 22, a second valve means shown here as a second ball-type check valve assembly 76 of standard construction, will be urged into the closed position shown in FIG. 3.

Upon patient inhalation, check valve assembly 76 will open permitting air to enter expansion chamber 28 in the direction of the arrows identified by the numerals 77 in FIG. 3. This air will mix with the particulate laden mist and will flow upwardly of the device through passageway 42a where it will impinge upon diaphragm 44 causing it to move pivotally about pivot point P into the open position shown in FIG. 3. As the mixture of air and particulate laden mist enters chamber 38, first valve means 36 will be urged into its closed position and the particulate laden mist and air mixture will enter flexible conduit 32 for flow in the direction of the arrow 79 toward the patient.

An extremely important aspect of the apparatus of the present invention resides in the provisions of baffle means or baffle wall 50. This wall partially blocks entrance to chamber 36 and impedes the progression of the larger particles contained within the particulate laden mist as the mist tends to flow toward chamber 38. Baffle wall 50 is strategically located and designed so that the larger particles, contained within the particulate laden mist, will be unable to pass over the barrier and will fall by force of gravity into chamber 28. This important aspect of the invention prevents the undesirable flow of larger particles of medicament toward the patient via chamber 38.

When the patient exhales, check valve 36 will move into the open position shown by the phantom lines in FIG. 3 permitting the exhaled breath to enter filter assembly 16 where it is completely filtered by filter element 54 prior to entering the atmosphere via outlet port 16a of filter assembly 16. With this unique construction, upon patient exhalation the flexible diaphragm member 44 of flow control means 40 will close, blocking fluid flow through opening 42a. Accordingly, if the MDI is actuated during the time of patient exhalation the aeosolized medicament is constrained within expansion chamber 28 for use during the next sequential patient inhalation. Thus medicament chamber 28 functions both as a holding chamber and as a settling means thereby maximizing operationally efficiency and eliminating patient concern as to the timing of medication release from the MDI device.

Figure 9:
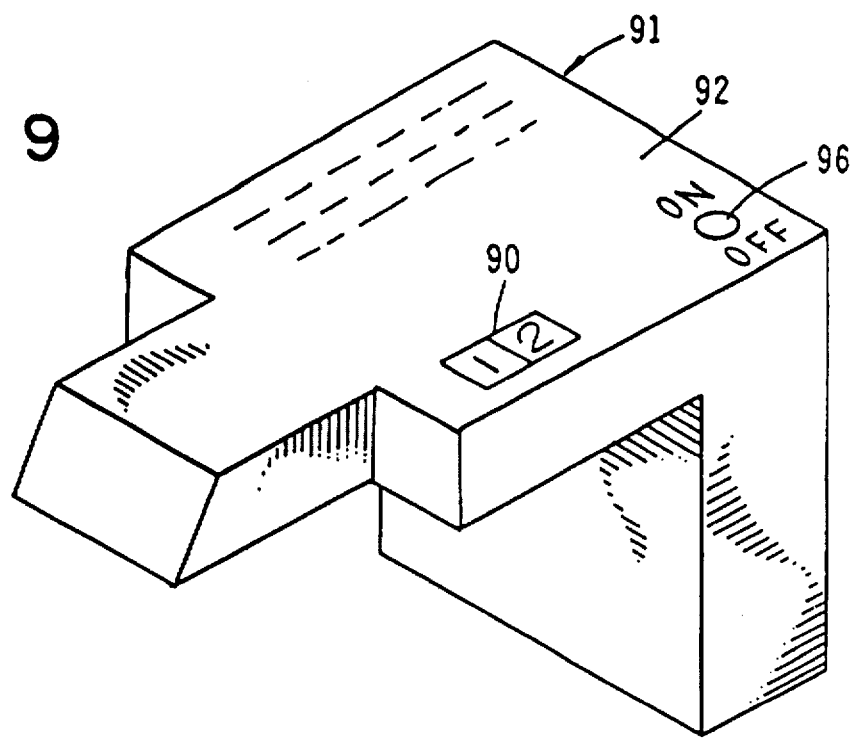
FIG. 9 is a generally perspective view of the breath-actuated release control attachment of the alternate form of the apparatus.
Figure 10:
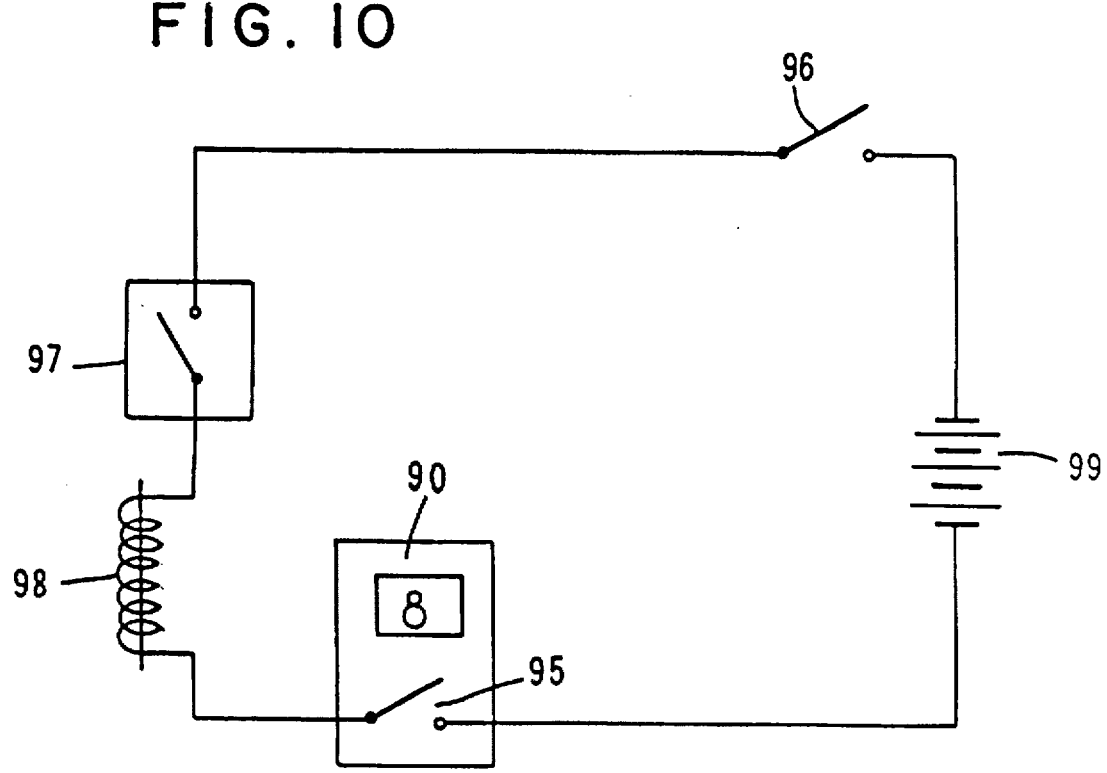
FIG. 10 is a simplified, generally schematic view of the breath-actuated release control circuit of the apparatus shown in FIG. 9.
Figure 11:
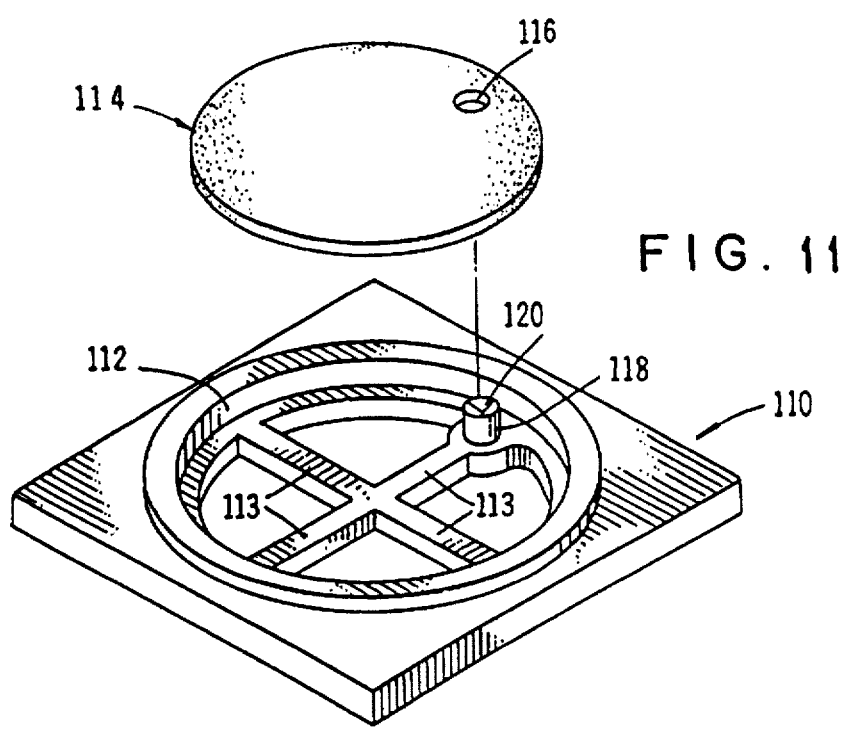
FIG. 11 is a generally perspective, exploded view of an alternate form of valve assembly of the invention.
Figure 12:
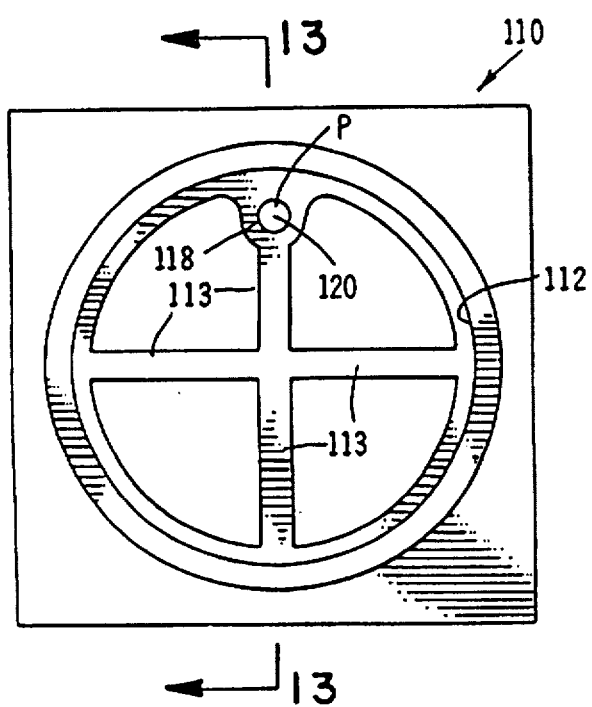
FIG. 12 is a top plan view of the valve base shown in FIG. 11.
Figure 13:
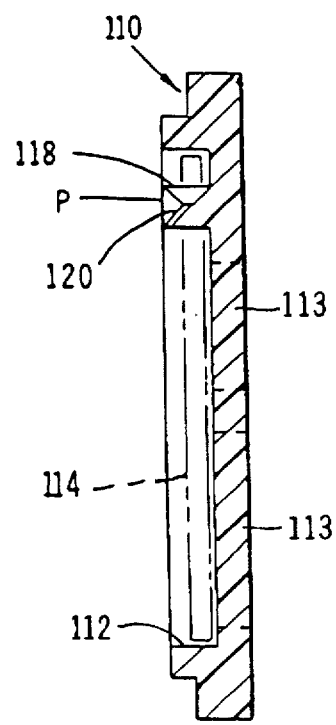
FIG. 13 is a cross-sectional view taken along lines 13—13 of FIG. 12.
Figure 14:
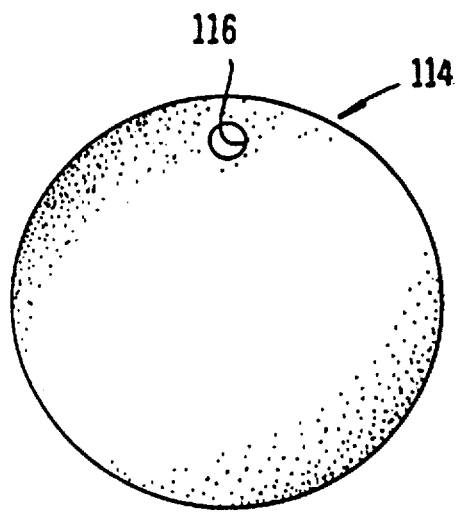
FIG. 14 is a top plan view of the valve member of the valve assembly shown in FIG. 11.

Referring now to FIGS. 8, 9, and 10, an alternate form of inhalation apparatus of the invention is there illustrated. This alternate form of the invention is similar in many respects to that shown in FIGS. 1 through 5, and like numbers have been used to identify like components. A major difference between this latest form of the invention and that earlier described comprises the addition of a breath-actuated means for automatically releasing a metered dose of medicament laden spray from the MDI into the expansion chamber 28. This novel breath actuated means includes a presetable declining counter 90 which stops all dose release functions upon the counter reaching zero. In instances where closely defined patient prescribed doses require multiple actuations of the MDI, this system is extremely beneficial in the prevention of both under dosing and over dosing of the patient.

As best seen in FIGS. 8 and 9, the breath actuated means of the invention is here provided in the form of an actuation subassembly 91 which includes a hollow housing 92 which is removably connected to main housing 14 in the manner best seen in FIG. 8. Disposed within housing 92 is a counter means of conventional construction which includes a counter 90 that can be preset to the desired number of inhaler actuations. An "on/off" switch 96 is mounted on housing 92, and when in the "on" position, will cause exhalation by the patient into chamber 22 to actuate a pressure activated switch means or switch 97 (FIG. 10) which communicates with chamber 38 via flow passageway 92a (FIG. 8). Actuation switch 97 will cause a solenoid 98, which is interconnected therewith (FIG. 10), to be energized by a source of electricity such as a battery 99. Energization of solenoid 98 will cause an actuator assembly 100, to which it is operably connected, to move from an at rest first position shown by the solid lines of FIG. 8 to an activated position shown by the phantom lines in FIG. 8. As the actuator mechanism moves into the actuated position shown by the phantom lines in FIG. 8, a downwardly extending protuberance 100a provided on arm 100b of the actuating mechanism will apply an operating pressure to the MDI canister 18 causing it to move downwardly within chamber 22 to the position shown by the phantom lines in FIG. 8. As the MDI canister is moved downwardly, the aerolized medication contained within the canister will be released through stem 24 and will flow into chamber 28 via passageway 68a.

Upon each actuation of the solenoid 98, the counter-reading is automatically reduced by one. The circuitry of the device is such that completion of the desired number of patient inhalations and exhalations, counter 90 will reach zero causing switch 95 to open. Opening of switch 95 prevents further delivery of medication until the counter and on/off switch have been reset.

It is to be understood that a wide variety of actuating mechanisms other than that shown in the drawings could be used to depress the MDI canister. For example, a small electric motor could be used instead of the solenoid device and a variety of actuating mechanisms could be interconnected with the electric motor or with a solenoid to accomplish the desired function.

Turning next to FIGS. 11 through 18, alternate forms of the flow control means of the invention are there illustrated. Referring particularly to FIGS. 11 through 15, one alternate form of the flow control means comprises a generally rectangular planar base 110 having a recessed opening 112 for receiving therewithin valve member 114. Coplanar crossing support struts 113 span opening 112 for engagement with valve member 114 when the valve is in a closed configuration. Valve member 114, which is a generally planar, yieldably deformable, elastomeric member is provided with a circular aperture 116 located proximate its outer periphery. In the assembly of valve member 114 with base 110, aperture 116 is emplaced over a generally cylindrically shaped, upstanding pin 118 which defines a pivot point P and which is preferably integrally formed with base 100. The end of cylindrical pin 118a is provided with an angular shaped indentation 120 for use in staking member 114 to base 110. The valve assembly as thusly assembled can be placed into the desired chamber, such as chamber 38 (FIG. 3), to directionally control fluid flow therethrough.

Figure 15:
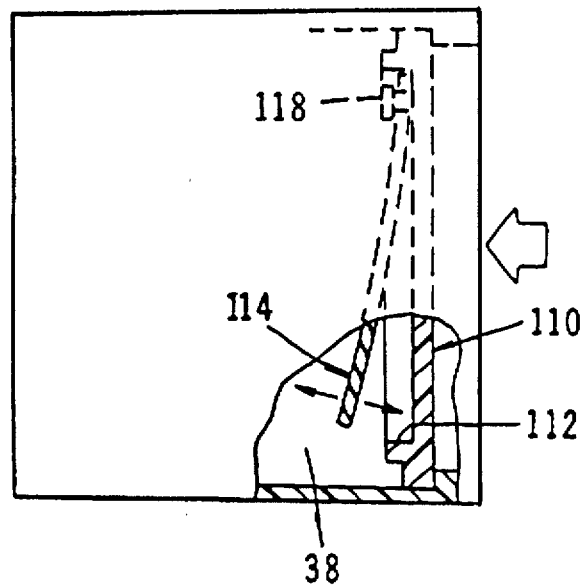
FIG. 15 is a generally diagrammatic, side-elevational view showing the valve assembly of this latest form of invention positioned within a fluid flow passageway.

As air or aerosol mist flows through passageway 28a, the edge-pinned valve member 114 opens in the manner indicated in FIG. 15 by pivoting about pin 118. Only a minimal resistance to the valve opening is created by the valve material as it flexes at its highly novel single point of attachment. When an aerosol-laden medication containing mist is flowing through the valve, the flow restriction is considerably less than that exhibited by the prior art center-pin mounted valve construction, thereby avoiding any undesirable recombining and settling of particles as occurs in prior art devices wherein a substantial amount of medication is lost and not available for patient treatment.

It is to be understood that while 110 is shown as generally rectangular in shape, the base could be constructed in a circular rather than square configuration for easy mounting within medical tubing, or devices having tubular shaped flow passageways.

Figure 16:
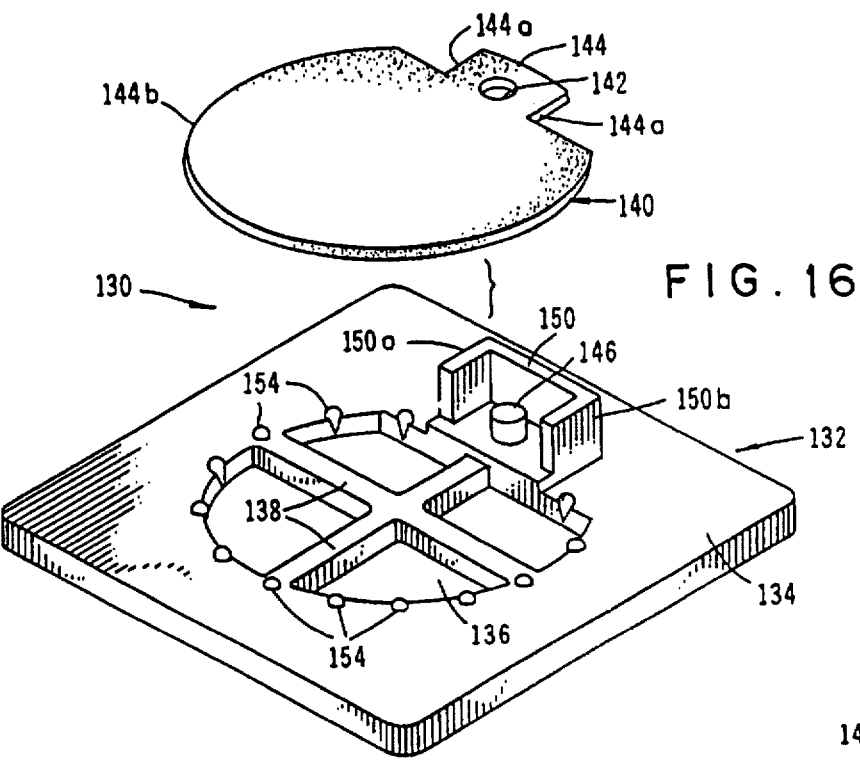
FIG. 16 is a generally perspective, exploded view of still another form of valve assembly of the invention.
Figure 17:
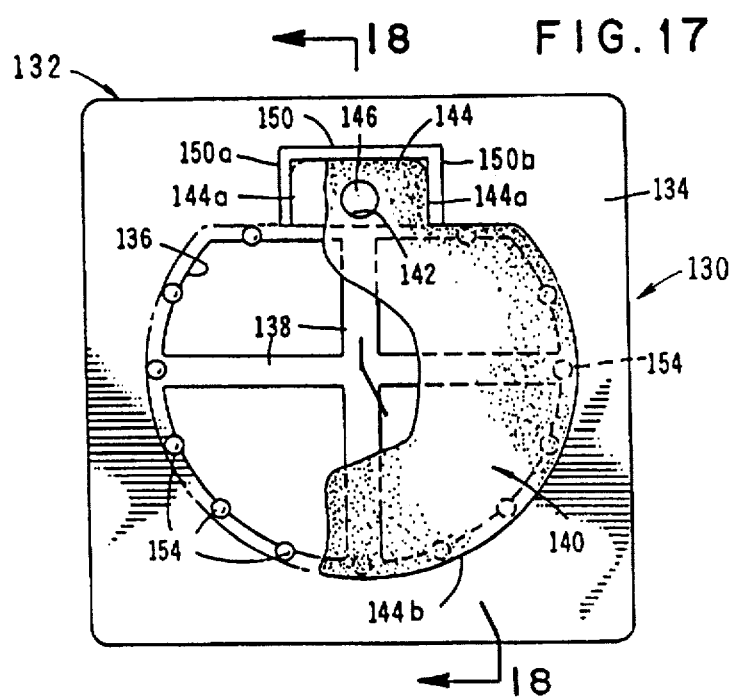
FIG. 17 is a top plan view of the form of valve assembly shown in FIG. 16.
Figure 18:
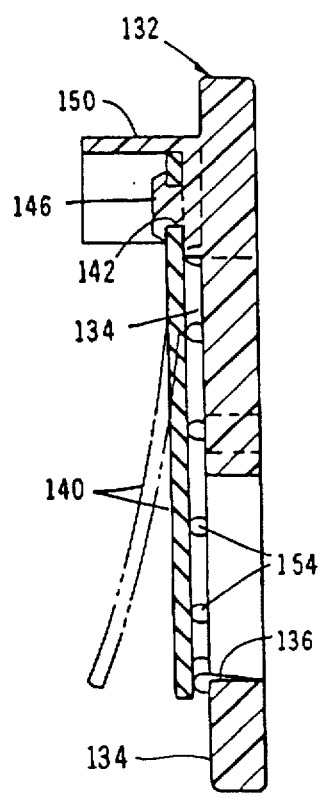
FIG. 18 is a cross-sectional view taken along lines 18—18 of FIG. 17.
Figure 19:
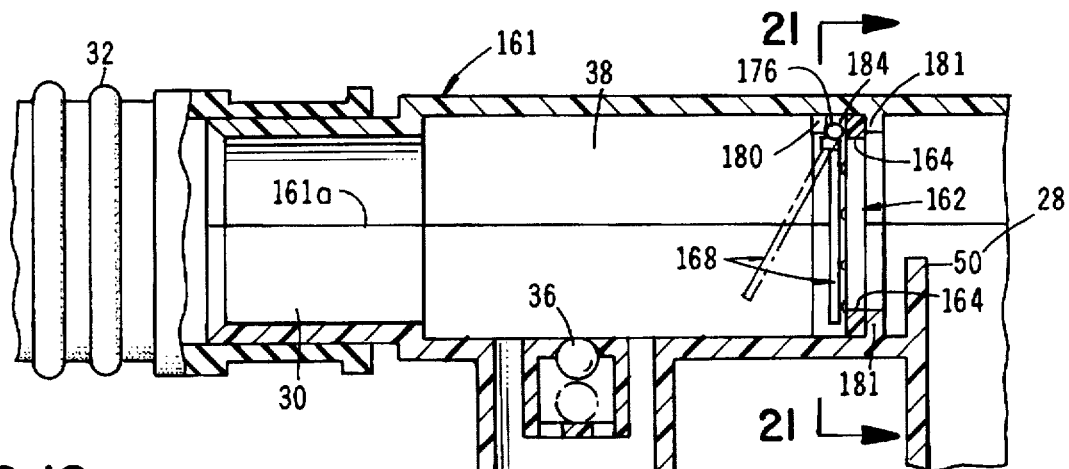
FIG. 19 is an enlarged, fragmentary, cross-sectional view of the forward portion of an alternate embodiment of the inhalation apparatus of the invention in which a different type of valve assembly is utilized.

Turning now to FIGS. 16, 17, and 18, an alternate form of the valve construction of the present invention is there shown and generally designated by the numeral 130. The valve of this latter form of the invention comprises a generally square planar base 132 having a generally planar face 134 provided with an opening 136. Coplanar crossing support struts 138 span opening 136 for engagement with a pivotally mounted valve member 140. Valve member 140 comprises a generally planar, yieldably deformable, elastomeric member having a circular aperture 142 located within a tab like extension 144 which is defined by parallel sides 144a and an arcuate segment 144b. In the assembly of valve member 140 to base 132, aperture 142 is emplaced over a generally cylindrically shaped, upstanding pin 146 which is preferably integrally formed with base 132, and pressed down into place.

When the valve member 140 is in position over pin 146 in the manner shown in FIG. 17, tab-like extension 144 is closely received within an upstanding walled structure 150 provided on base 132 and extending outwardly from face 134. Structure 150 includes spaced-apart walls 150a and 150b which are spaced apart by a distance slightly greater than the distance between sides 144a of segment 144. With this construction, valve member 140 is prevented from rotating relative to base 132 during its pivotal movement between a valve open and a valve closed position.

When the valve assembly is assembled in the manner described in the preceding paragraph it can be placed into the desired breathing passageway, such as passageway 38 to directionally control fluid flow through the passageway. As air or aerosol mist flow through conduit 38, the edge pinned valve member 140 opens and closes by pivoting about pin 146. A very minimal resistance to valve opening and closing is created by the valve material as it flexes along the width of tab 144. To prevent surface tension from impeding the valve opening, a plurality of circumferentially spaced, upstanding dimples 154 are provided on face 134 of base 132 proximate opening 136.

As before, when an aerosol-laden medication containing mist is flowing through the valve, the flow restriction is so small that undesirable recombining and settling of particles is effectively prevented so that medication is not lost and continues to be available for patient treatment.

Referring next to FIGS. 19 through 22, still another form of flow control means of the invention is there illustrated and generally designated by the numeral 160. This flow control means is usable with a sectionalized main housing 161 which is substantially identical to housing 14 and like numbers are used in FIG. 19 to identify like components. More particularly, the housing shown in FIG. 17 comprises a breathing port 30 which is coupled with the patient via a flexible conduit 32. As before, the device includes valve means 36 of the character previously described which controls flow from a second chamber 28 toward a first chamber 38. Disposed between chambers 28 and 38 is a baffle means shown as a wall 50. Disposed between wall 50 and chamber 38 is the flow control means of this latest form of the invention.

Figure 20:
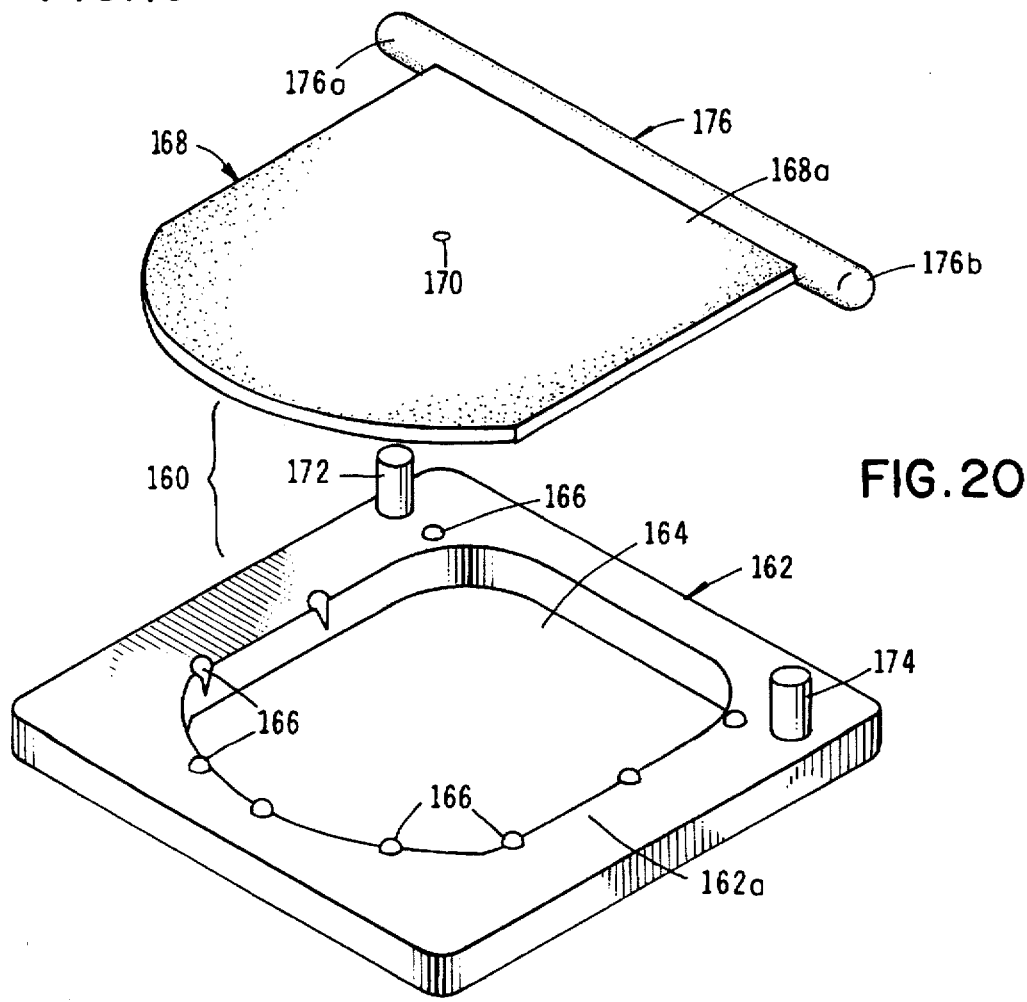
FIG. 20 is a generally perspective, exploded view of the alternate form of valve assembly shown in FIG. 19.
Figure 21:
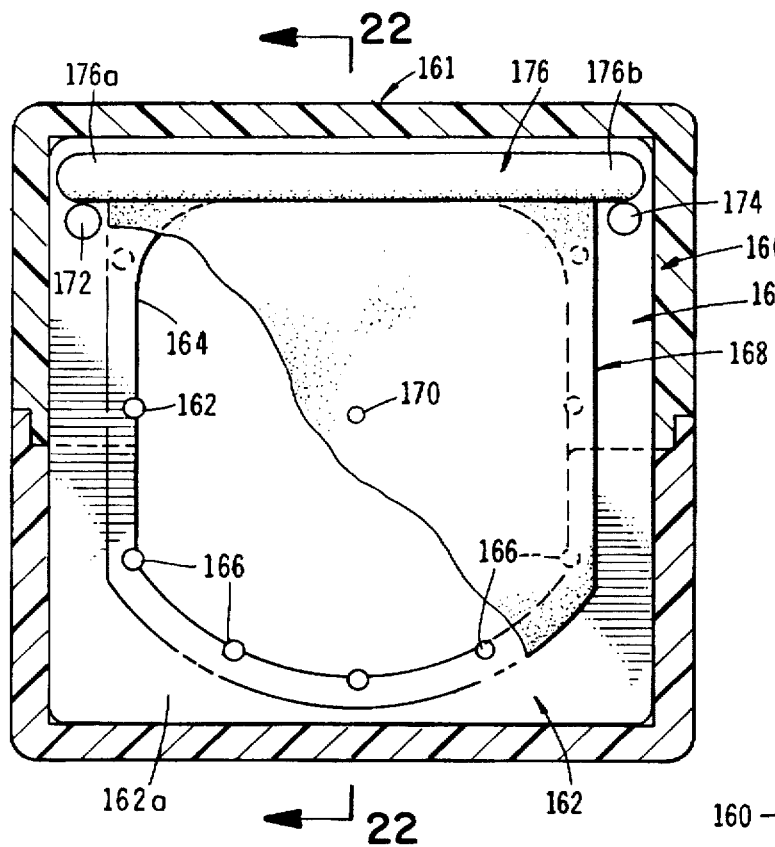
FIG. 21 is a cross-sectional view taken along lines 21—21 of FIG. 19.
Figure 22:
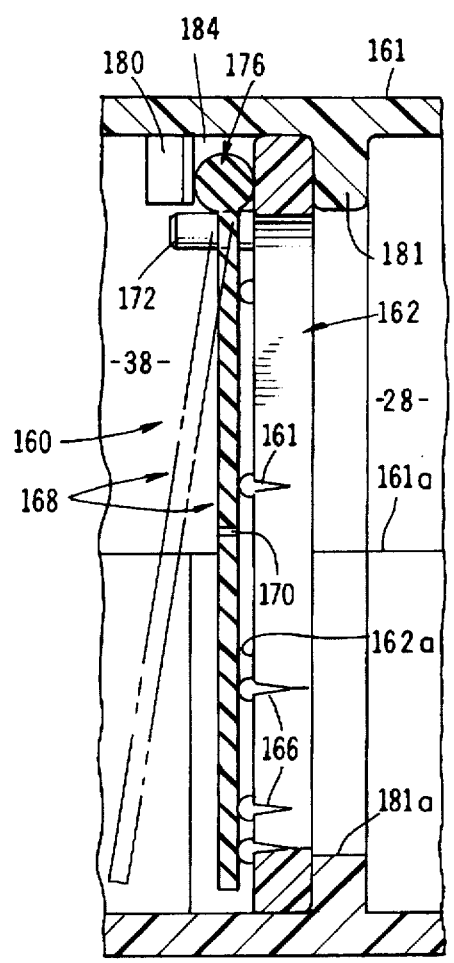
FIG. 22 is a cross-sectional view taken along lines 22—22 of FIG. 21.

Referring particularly to FIGS. 21 and 22, this latest form of the flow control means of the invention can be seen to comprise a generally rectangularly shaped planar base 162 having an opening 164 formed therein. As before, a plurality of circumferentially spaced, upstanding dimples 166 are provided on the upper surface 162a of base 162 and circumscribe opening 164 in the manner shown in FIGS. 20 and 21. When the valve member 168 of the flow control means of this latest form of the invention is closed, the valve member lightly engages dimples 166 in the manner shown in FIG. 22. As best seen in FIG. 20, valve member 168 is a generally planar, yieldably deformable, elastomeric member and in this instance is provided with a small, generally centrally located circular aperture 170.

Formed proximate the upper corners of base 162 are pivot defining means, here provided as upstanding support posts 172 and 174 which uniquely pivotally support valve member 168. More particularly, as shown in FIG. 20, a transverse pivot arm 176 spans the upper margin 168 of valve member 168 and has opposite end portions 176a and 176b which extend slightly outwardly from the valve member. When the valve member 168 is mated with base 162 in its operating position, end portions 176a and 176b of pivot arm 176 rest upon and are supported by support pins 172 and 174 respectively. To retain pivot bar 176 in position relative to base 162, capture means are formed on housing 161. These capture means here comprise radially inwardly extending tabs 180 (FIG. 19) which, in cooperation with a wall 181 provided on housing 161, define a space 184 within which a portion of base 162 and ends 176a and 176b of the pivot arm are held captive in the manner shown in FIG. 19. With this construction, pivot arm 176 is maintained in close proximity with base 162. Wall 181 is provided with an opening 181a which permits flow of medication laden mist toward passageway 38. Housing 162 is constructed in two parts which mate along a party line 161a so that the valve assembly can be positioned within the device in the manner shown.

When the valve assembly is mounted within housing 161 in the manner described in the preceding paragraph, it functions to directionally control fluid flow through passageway 38. As air or aerosol mist flows through passageway 38, valve member 168 open and closes in the manner shown by the phantom lines in FIG. 19. More particularly, the valve member 160, including pivot arm 176 pivots about pivot posts 172 and 174. A very minimal resistance to valve opening and closing is created by the substantially single line engagement between the curved surfaces of pivot posts 174 and the curved surface of the ends 176a and 176b of pivot arm 176. To prevent surface tension from impeding the valve opening, the plurality of circumferentially spaced, upstanding dimples 166 are provided on base 162 proximate opening 164 (see FIGS. 20 and 22).

As before, when an aerosol-laden medication containing mist is flowing through the valve, the flow restriction is so small that undesirable recombining and settling of particles is effectively prevented thereby precluding the undesirable loss of medication.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:
1. A fluid delivery apparatus comprising:
   (a) a housing having interconnecting first and second chambers;
   (b) means connected to said housing for introducing a fluid into said first chamber of said housing; and
   (c) flow control means carried by said housing for controlling passage of fluid between said first and second chambers, said flow control means comprising:
      (i) a base having an opening therethrough;
      (ii) pivot defining means connected to said base proximate said opening comprising a pair of outwardly extending pivot posts defining a pair of spaced-apart pivot points; and
      (iii) a valve member pivotally movable relative to said pivot-defining means between a first position wherein said valve member is superimposed over said opening to a second valve open position wherein said valve member is spaced apart from said opening to a second valve open position, said valve member including a pivot arm having end portions pivotally supported by said outwardly extending pivot posts.

2. An apparatus as described in claim 1 in which said housing further comprises capture means for maintaining said pivot arm of said valve member in close proximity with said base of said flow control means.

3. An apparatus as described in claim 2 in which said capture means comprises at least one radially inwardly extending tab formed on said housing for defining a pivot arm receiving space between said base of said flow control means and said tab.

4. An apparatus as defined in claim 2 in which said base further includes a plurality of small dimples circumscribing said opening in said base of said flow control means.

5. An apparatus as defined in claim 2 in which said valve member is provided with at least one aperture therethrough.

6. An apparatus as defined in claim 2 in which said housing includes a radially inwardly extending tab and a wall having an opening therethrough, said wall being disposed between said first and second chambers and cooperating with said tab to define a valve receiving space for receiving a portion of said base of said flow control means and a portion of said pivot arm thereof.

7. An apparatus as defined in claim 2 in which said apparatus comprises an aerosol inhalation apparatus and in which said means for introducing fluid into said first chamber comprises means for delivering a particulate-laden spray into said first chamber.

8. An aerosol inhalation apparatus for delivering a medicament containing mist to a patient comprising:
   (a) a housing having interconnecting first and second chambers and including a wall disposed between said first and second chambers, said wall having an opening therein;
   (b) medication means connected to said housing for introducing into said first chamber of said housing a particulate-laden spray having large and small particles of medicament;
   (c) inhalation means connected to said housing for communication with said second chamber for permitting the patient to inhale particulate-laden spray residing within said housing and to exhale a portion thereof into said second chamber;
   (c) flow control means carried by said housing for controlling passage of particulate-laden spray between said first and second chambers during patient inhalation and exhalation, said flow control means comprising:

(i) a base having an opening therethrough;

(ii) pivot defining means connected to said base proximate said opening comprising a pair of outwardly extending pivot posts defining a pair of spaced-apart pivot points; and (iii) a valve member pivotally movable relative to said pivot-defining means between a first position wherein said valve member is superimposed over said opening to a second valve open position wherein said valve member is spaced apart from said opening to a second valve open position, said valve member including a pivot arm having end portions pivotally supported by said outwardly extending pivot posts.

9. An aerosol inhalation apparatus as described in claim 8 in which said housing further comprises capture means for maintaining said pivot arm of said valve member in close proximity with said base of said flow control means.

10. An apparatus as described in claim 9 in which said capture means comprises at least one radially inwardly extending tab formed on said housing for defining a pivot arm receiving spaced between said base of said flow control means and said tab.

11. An apparatus as defined in claim 9 in which said base further includes a plurality of small dimples circumscribing said opening in said base of said flow control means.

12. An apparatus as defined in claim 9 in which said valve member is provided with at least one aperture therethrough.

13. A valving mechanism for controlling passage of fluids between first and second chambers of a housing, said valving mechanism comprising:

(a) a base having an opening therethrough, said base being mounted within the housing between the first and second chambers;

(b) pivot defining means connected to said base proximate said opening comprising a pair of outwardly extending pivot posts defining a pair of spaced-apart pivot points; and (c) a valve member pivotally movable relative to said pivot-defining means between a first position wherein said valve member is superimposed over said opening to a second valve open position wherein said valve member is spaced apart from said opening to a second valve open position, said valve member including a pivot arm having end portions pivotally supported by said outwardly extending pivot posts.

14. A valve mechanism as described in claim 13 in which said base further includes a plurality of small dimples circumscribing said opening in said base of said flow control means.

15. A valving mechanism as defined in claim 13 in which said valve member is provided with at least one aperture therethrough.

16. A valving mechanism as defined in claim 15 in which said aperture is located generally centrally of said valve member.

17. A valving mechanism as defined in claim 16 in which said valve member is yieldably deformable.

18. A valving mechanism as defined in claim 17 in which said valve member comprises an elastomer.

\* \* \* \* \*